United States Patent
Flower

[11] Patent Number: 5,899,876
[45] Date of Patent: May 4, 1999

[54] MULTIPLE SITE DRUG DELIVERY SYSTEM

[75] Inventor: Ronald J. Flower, Lawrenceville, Ga.

[73] Assignee: Becton, Dickinson and Company, Franklin Lakes, N.J.

[21] Appl. No.: 08/921,915

[22] Filed: Aug. 27, 1997

[51] Int. Cl.$^6$ ..................................... A61N 1/30
[52] U.S. Cl. ............................. 604/20; 607/156
[58] Field of Search ................... 604/20, 21, 30, 604/151, 890.1; 607/152, 153, 156

[56] References Cited

U.S. PATENT DOCUMENTS

| | | | |
|---|---|---|---|
| 4,856,188 | 8/1989 | Sibalis | 604/20 |
| 5,135,478 | 8/1992 | Sibalis | 604/20 |
| 5,254,081 | 10/1993 | Maurer et al. | 604/20 |
| 5,358,483 | 10/1994 | Sibalis | 604/20 |
| 5,421,817 | 6/1995 | Liss et al. | 604/20 |
| 5,551,953 | 9/1996 | Lattin et al. | 604/20 |

FOREIGN PATENT DOCUMENTS

| | | | |
|---|---|---|---|
| B-68330/90 | 6/1991 | Australia | 604/20 |
| WO 91/15261 | 10/1991 | WIPO | 604/20 |

*Primary Examiner*—Wynn Wood Coggins
*Assistant Examiner*—Sharon Finkel
*Attorney, Agent, or Firm*—Arthur D. Dawson; Susan A. Capello; Allen W. Wark

[57] ABSTRACT

An apparatus and method of delivering drugs from multiple sites on a patients body is provided. A controller is used at each site, and these controllers communicate with each other to coordinate drug delivery from the multiple sites. In a preferred embodiment, the drugs are delivered using iontophoresis.

24 Claims, 8 Drawing Sheets

MULTIPLE SITE DRUG DELIVERY SYSTEM

BACKGROUND OF THE INVENTION

1. Field of the Invention

The invention is in the field of drug delivery. In particular, the invention relates to drug delivery device capable of delivering one or more drugs to a patient from multiple sites of the patient's body, and coordinating the delivery of drugs at those sites. In the preferred embodiment of the invention, the delivery of drugs is accomplished by iontophoresis.

2. Description of Related Art

Iontophoresis is the application of an electrical current to transport ions through intact skin. One particularly advantageous application of iontophoresis is the non-invasive transdermal delivery of ionized drugs or other therapeutic agents into a patient. This is done by applying low levels of current to a patch placed on the patient's skin, which forces the ionized drugs contained in the patch through the patient's skin and, if desired, into his or her bloodstream for system or delivery. Because the amount of drug delivered is related to the amount of current applied, the drug delivery rate can be precisely controlled by controlling the current.

An iontophoretic drug delivery system typically includes a current source, such as a battery and current controller, and a patch. The patch includes an active reservoir and a return reservoir. The active reservoir contains the ionized drug. The return reservoir typically contains a saline gel and collects ions emanating from the patient's skin when the drug is being delivered into the patient's skin. The patch also has two electrodes, each arranged inside the active and return reservoirs to be in respective contact with the drug and saline. The anode (positive electrode) and the cathode (negative electrode) are respectively electrically connected to the anode and cathode of the current source by electrical conductors. Either the anode or the cathode is arranged within the drug reservoir, depending on the charge of the ionized drug, and is designated the active electrode. The other electrode is arranged within the return reservoir, and is designated the return electrode.

When current from the current source is supplied to the active electrode, the drug ions migrate from the drug gel in the reservoir toward and through the skin of the patient. At the same time, ions flow from the patient's skin into the saline solution of the return reservoir. Charge is transferred into the return electrode and back to the current source, completing the iontophoretic circuit. The electronic controller controls the current source so that drug delivery is accomplished at a constant or varying rate, or over a short, long or periodic time interval. This controller generally requires relatively complex electrical circuitry, and may include a microprocessor, to meet the current delivery requirements.

A single electronic controller and patch is suitable for the delivery of a single drug to the patient. When multiple drugs are to be delivered simultaneously, and those drugs can be delivered safely together, multiple patches, each patch containing a separate drug, may be used with respective multiple controllers.

In certain cases, however, the administration of different drugs from multiple patches simultaneously may be contraindicated. In other cases, the simultaneous administration of different drugs may be required to attain a desired therapeutic effect or to counteract an undesirable side effect. In either case, coordination among the multiple patches is required when delivering different drugs.

In addition, multiple patches may also be used to deliver a single drug from multiple sites on a patient's body. This would be advantageous, for example, when the current needed to deliver the desired drug dosage from a single patch would be high enough to cause discomfort to the patient. In this case, it would be desirable to deliver the drug from multiple patches, using a smaller dosage and thus a lower current at each patch. When multiple patches are used to deliver a single drug, it becomes important to coordinate the delivery from each patch to achieve the overall desired dosage.

Multiple patches may also be needed to deliver uninterruptedly a controlled drug dosage, for example, when the drug is needed for a life sustaining function. In this case, multiple patches are required because failure of a single patch would interrupt the delivery of the drug. By coordinating delivery of the drug from multiple patches, a failure at any one patch could be compensated for by increasing the current (and thus the drug dosage) of the other operative patches.

In all of the above cases, the delivery of a single drug or multiple drugs from multiple patches must be coordinated. Existing independent electronic controllers, however, do not have the capability of providing this coordination.

SUMMARY OF THE INVENTION

The present invention advantageously provides a method and apparatus for coordinating the delivery of drugs from multiple sites on a patient's body.

In one aspect of the invention, an apparatus for delivering drugs to a patient is provided. This apparatus includes a master controller with a transmitter that transmits commands into a first area of skin of the patient. The commands travel along the patient's skin to a second area of skin. This apparatus also includes a slave unit which receives the commands and controls the delivery of a drug in accordance with the received commands.

In another aspect of the invention, another apparatus for delivering drugs to a patient is provided. This apparatus includes a first unit including a first drug delivery device and an associated first controller, and a second unit including a second drug delivery device and an associated second controller. The second controller selectively communicates with the first controller via signals that travel between the controllers.

In yet another aspect of the invention, another apparatus for delivering drugs to a patient is provided. This apparatus includes a drug delivery device that is affixable to an area of skin of the patient, a controller for controlling the delivery of drugs from the drug delivery device, a transmitter for transmitting commands that travel along the patient's skin to other areas of skin, and a receiver for receiving commands transmitted by other apparatuses.

Yet another aspect of the invention is directed to a method of delivering drugs to a patient from multiple sites on the patient's body. This method is related to the apparatuses mentioned above.

BRIEF DESCRIPTION OF THE DRAWINGS

These and other features and advantages of the present invention can be understood by reference to the detailed description of the preferred embodiments set forth below taken with the drawings, in which.

DETAILED DESCRIPTION OF THE PREFERRED EMBODIMENTS

The invention is preferably implemented using iontophoretic drug delivery devices, although the present invention may also be applied to coordinating the drug delivery among other electronically-controlled drug delivery devices.

Figure 1:
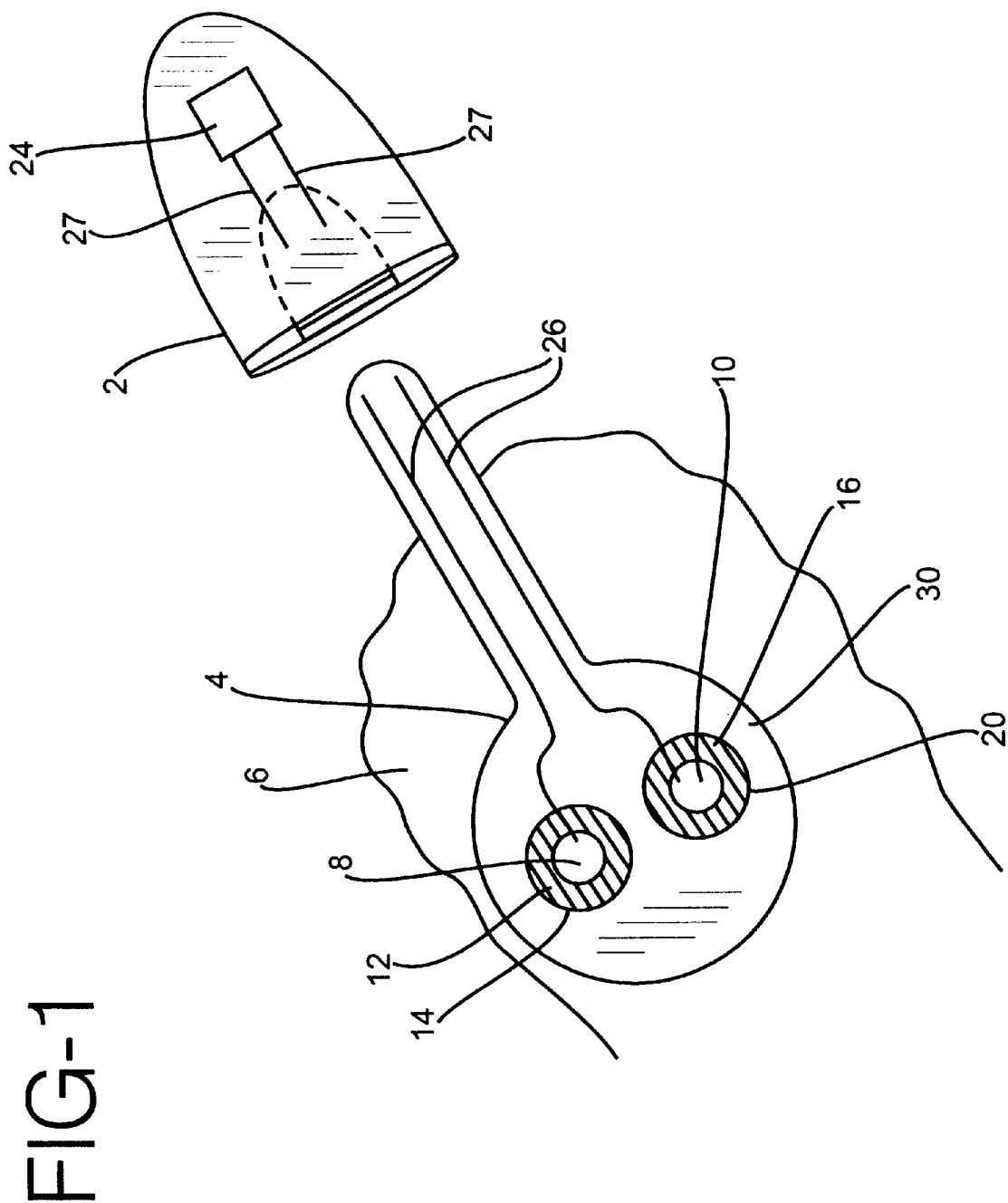
FIG. 1 is a perspective view of an iontophoretic drug delivery device.

One suitable type of iontophoretic drug delivery device includes a separate, reusable electronic current controller 2, which can be removably and electrically connected to a patch 4 containing the drug, therapeutic agent or medicament, as shown in FIG. 1. The patch 4 is attached to the skin of the patient 6. The patch includes an active electrode 8 and a return electrode 10, with the ionic drug 12 and active electrode 8 positioned within the active reservoir 14, and the saline or electrolyte 16 and return electrode 10 positioned within the return reservoir 20.

The patch 4 is generally a planar flexible member formed of, for example, a biocompatible material such as woven or non-woven textiles or polymers, or any other construction well-known in the art. The patch is attached to the patient's skin using adhesives or a strap or both. The patch includes an enlarged patch body 30, which includes the active and return reservoirs.

Figure 2:
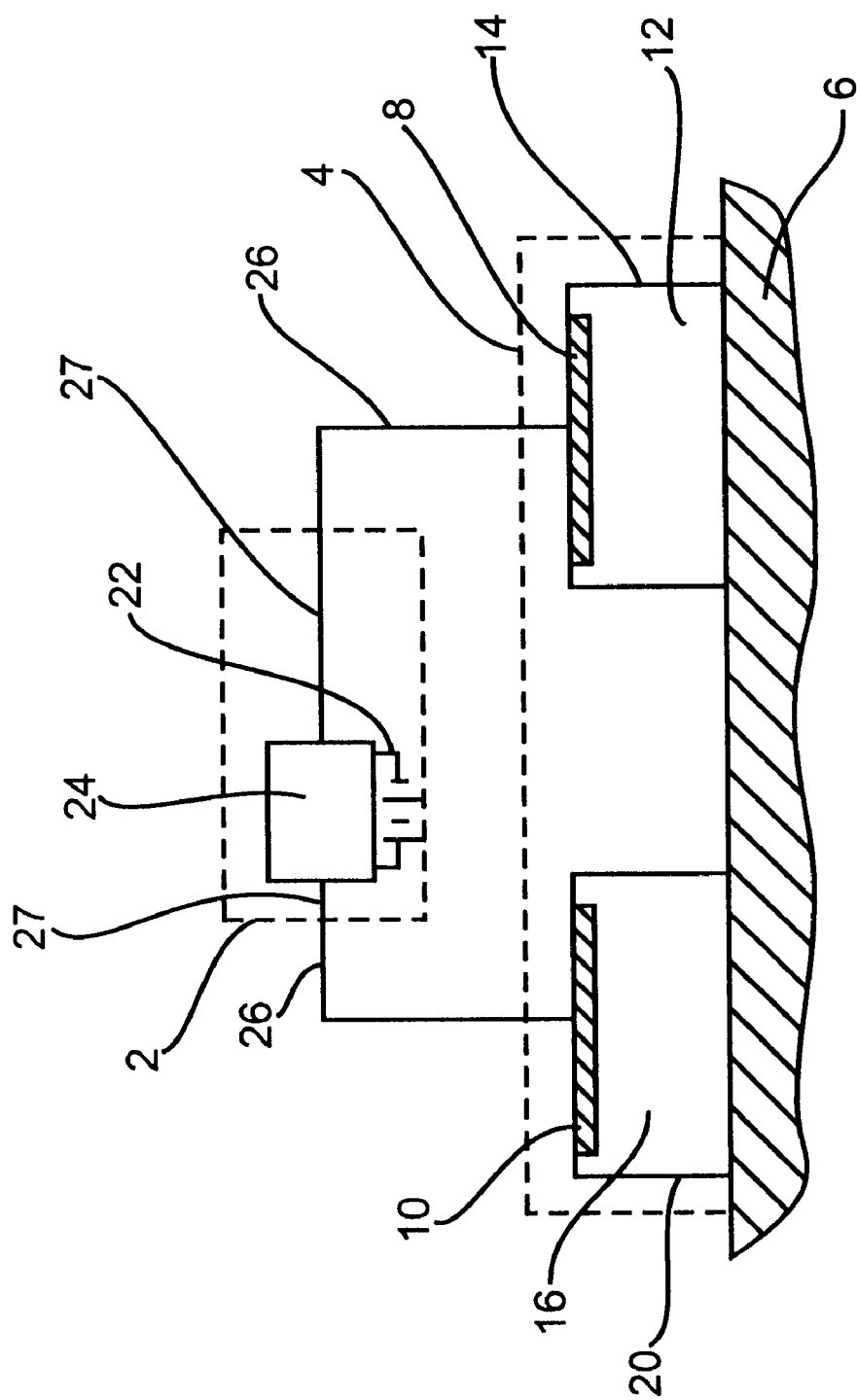
FIG. 2 is a block diagram of an iontophoretic drug delivery device.

The controller 2 has a power supply 22 and electronic control circuitry 24, as shown in FIG. 2. The controller is electrically coupled to the patch 4 using electronic interconnectors 26 and 27, such as a printed flexible circuit, metal foils, wires, tabs or electrically conductive adhesives. The power supply 22 in combination with the electrodes 8 and 10 and the patient's body 6 completes the iontophoretic circuit and generates an electric field across the body surface or skin on which the iontophoretic device is applied. The electric field causes the drug in the active reservoir 14 to be delivered into the body of the patient by iontophoresis.

The lower surface of the reservoirs are placed in contact with the skin. The electrodes are positioned so that an ionic current path is established between the electrodes 8 and 10 through the reservoirs and the patient's skin 6. Electrodes 8 and 10 are placed in conductive contact with the gels 12 and 16, respectively. A direct current source may be connected to the electrodes 8 and 10 so that the active electrode has the same charge polarity as the ionic drug 12. When current is passed through the active electrode 8 to the return electrode 10 through the skin 6, the ionic drug 12 contained in the active reservoir 14 is delivered through the skin 6 and into the patient.

Figure 3:
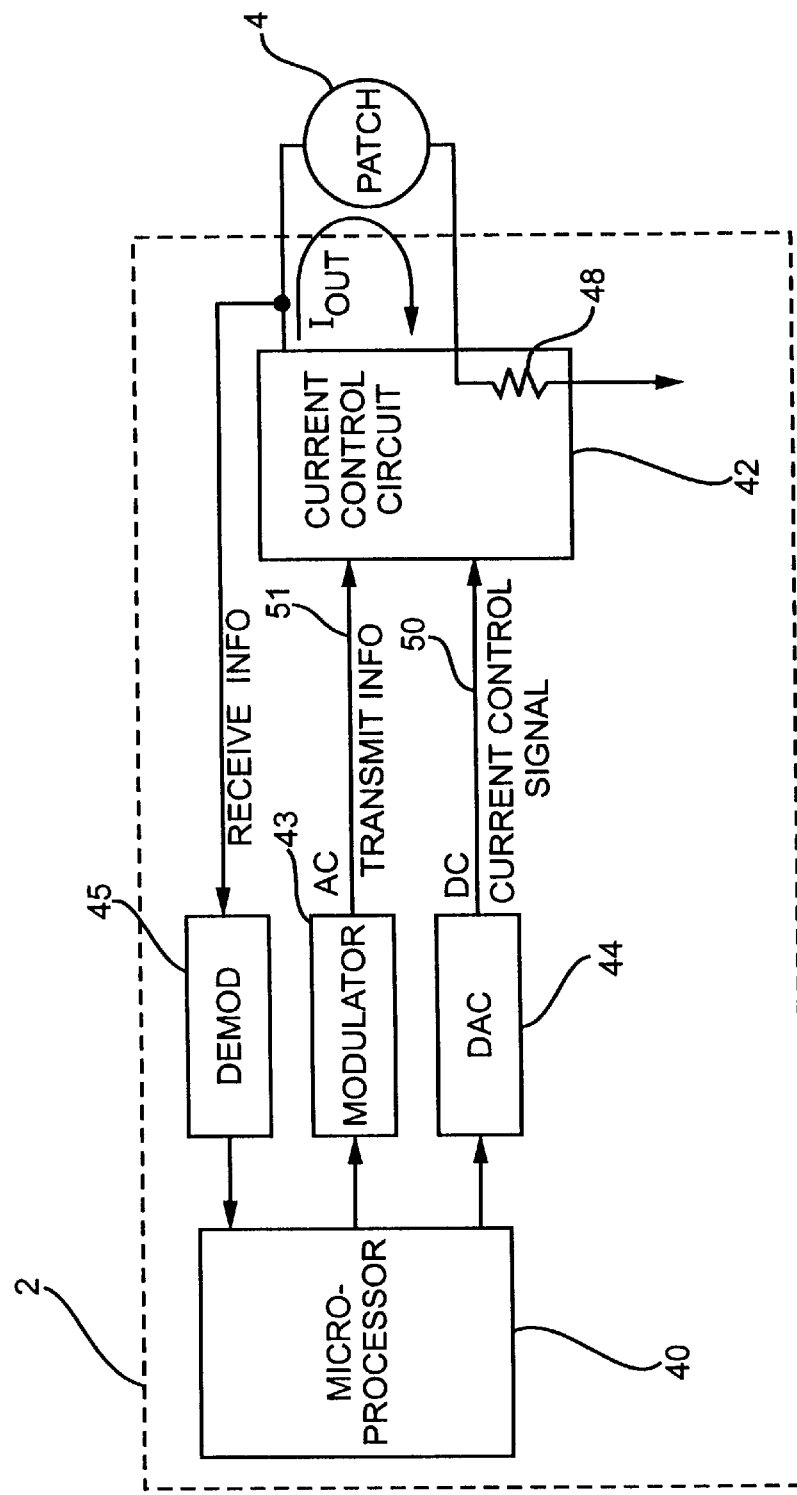
FIG. 3 is a block diagram of one embodiment of an iontophoretic controller.

FIG. 3 depicts a controller 2 that may be used as either a master controller, a slave controller, or as a multi-master controller, as explained below. The controller 2 may include, but is not limited to, a microprocessor 40, a digital-to-analog converter (DAC) 44, and a current control circuit 42. The microprocessor 40 sends a digital signal to the DAC 44, which converts the digital signal to an analog signal 50. This analog signal 50 controls the current control circuit 42 which ensures that the required amount of DC current is delivered to the patch 4 so that the correct amount of drug is delivered to the patient. The current control circuit 42 will produce the required DC output current irrespective of the varying impedance and/or capacitance of the load, including the patient's skin, the impedance of which normally varies from patient to patient and which may change as iontophoresis takes place.

Further, voltage from a sensor, such as a current sense resistor 48, is monitored by the current control circuit 42 to ensure that the DC component of the delivered current is correct. The current passing through the current sense resistor 48 is the same current actually being delivered through the iontophoretic patch and the skin. If an amount of DC current actually delivered is less than or greater than the required DC current, the current control circuit 42 adjusts the DC current to the required level.

In addition to controlling the DC current, the controller also includes a transmitter for transmitting information into the patient's skin through the patch 4. In this embodiment, the transmitter comprises the modulator 43 and the current control circuit 42. The modulator 43 modulates an AC carrier with information from the microprocessor 40 resulting in a modulated carrier signal 51. This signal 51 is supplied to the current control circuit 42. The current control circuit 42 superposes the modulated carrier signal 51 with the DC current being delivered to the patch 4. The current flowing through the patch 4 therefore contains a DC component and an AC component. The DC component causes the drugs to be delivered into the patient's body via iontophoresis, as described above. When the carrier frequency of the AC component of the current is greater than approximately 1000 Hz, the AC component will be conducted by the patient's skin so that the signal will travel along the patient's skin. As a result, the modulated AC carrier signal can be received at all areas of the patient's body. This AC carrier signal does not, however, contribute to the delivery of drugs because the average value of the AC signal is zero. The voltage of the AC component applied to the patch is preferably between 50 and 500 mV.

The controller also includes a receiver. In this embodiment, the receiver comprises the demodulator 45. The receiver can receive the modulated AC carrier signals (transmitted by other controllers) from the patient's skin. The modulated AC carrier is demodulated by the demodulator 45, extracting the transmitted information. This information is digitized and sent to the microprocessor 40 where it is read. The microprocessor can then take appropriate controlling action, depending on the information that is received.

Numerous configurations of controllers located at different sites on a patient's body can be used. These configurations include, but are not limited to, a master-slave arrangement and a multi-master arrangement. Other arrangements can be readily envisioned. Various methods of interfacing and coordinating the multiple controllers are well known to those skilled in the art of computer architecture and network design.

Figure 4:
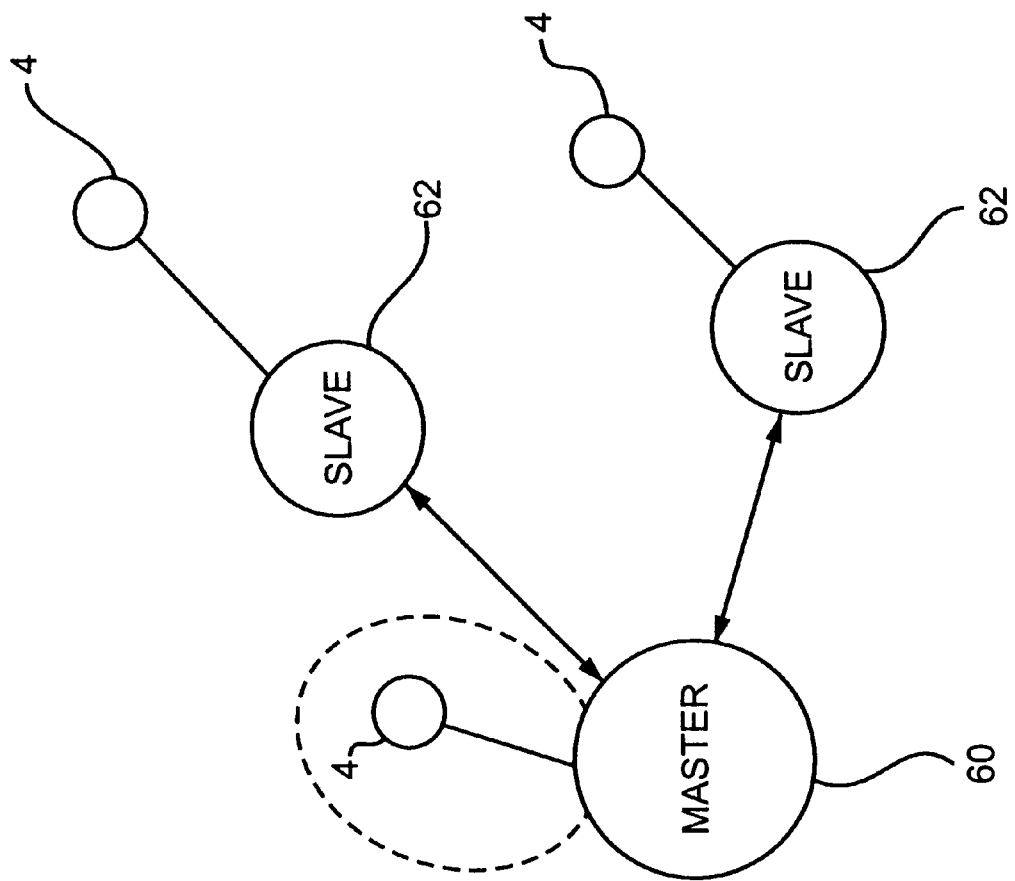
FIG. 4 is a diagram of a master-slave configuration of drug delivery devices.

FIG. 4 is a pictorial representation of a master-slave arrangement of controllers. The master controller unit 60 is located at a first area on the patient's skin. The slave units 62 are located at other areas on the patient's skin. Each of the slave units 62 has an iontophoretic patch 4 for delivering drugs to the patient. While FIG. 4 depicts one master unit and two slave units, any number of slave units can be used. A patch 4 controlled directly by the master controller 60 may also optionally be included. Once the master and slave units are affixed to the patient's body, the master unit transmits commands to one or more of the slave units instructing the slave units to deliver drugs and, optionally, to control the drug dosage by controlling the amount of current to be generated by the slave units.

In the embodiment depicted in FIG. 3, the slave units have the capability of transmitting information back to the master unit, and the master unit has the capability of receiving this information. By providing bi-directional communication, the embodiment can advantageously respond to changing conditions of the patient's body. For example, if an additional slave unit is affixed to the skin of the patient, the master unit 60 can recognize this condition, and instruct the slave unit to deliver drugs according to a desired pattern. Alternatively, if a slave unit 62 is removed from the patient's body, the master unit 60 can recognize this condition and adjust the operation of the remaining slave units accordingly.

Figure 5:
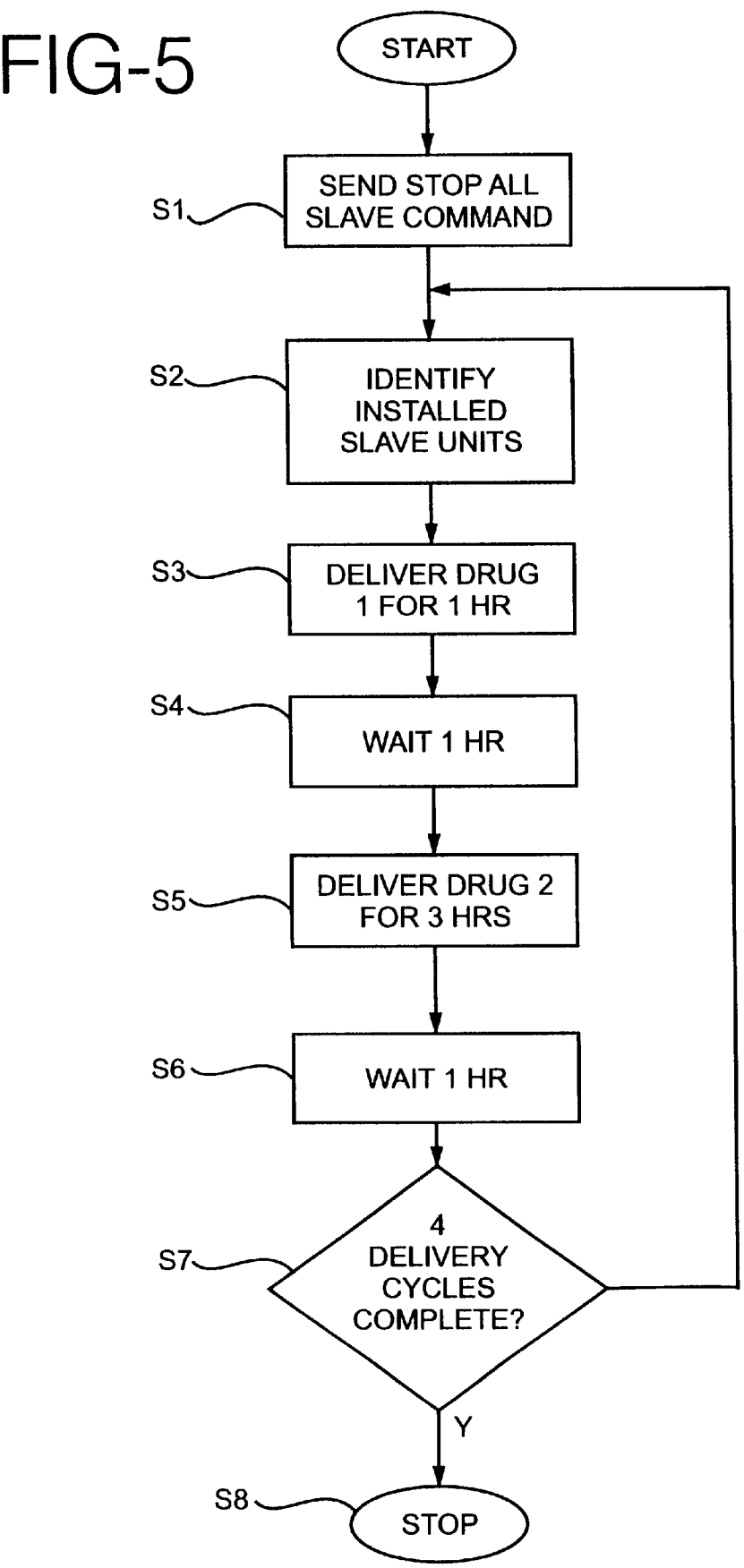
FIG. 5 is a flow chart depicting the operation of a master controller in a master-slave configuration.
Figure 6:
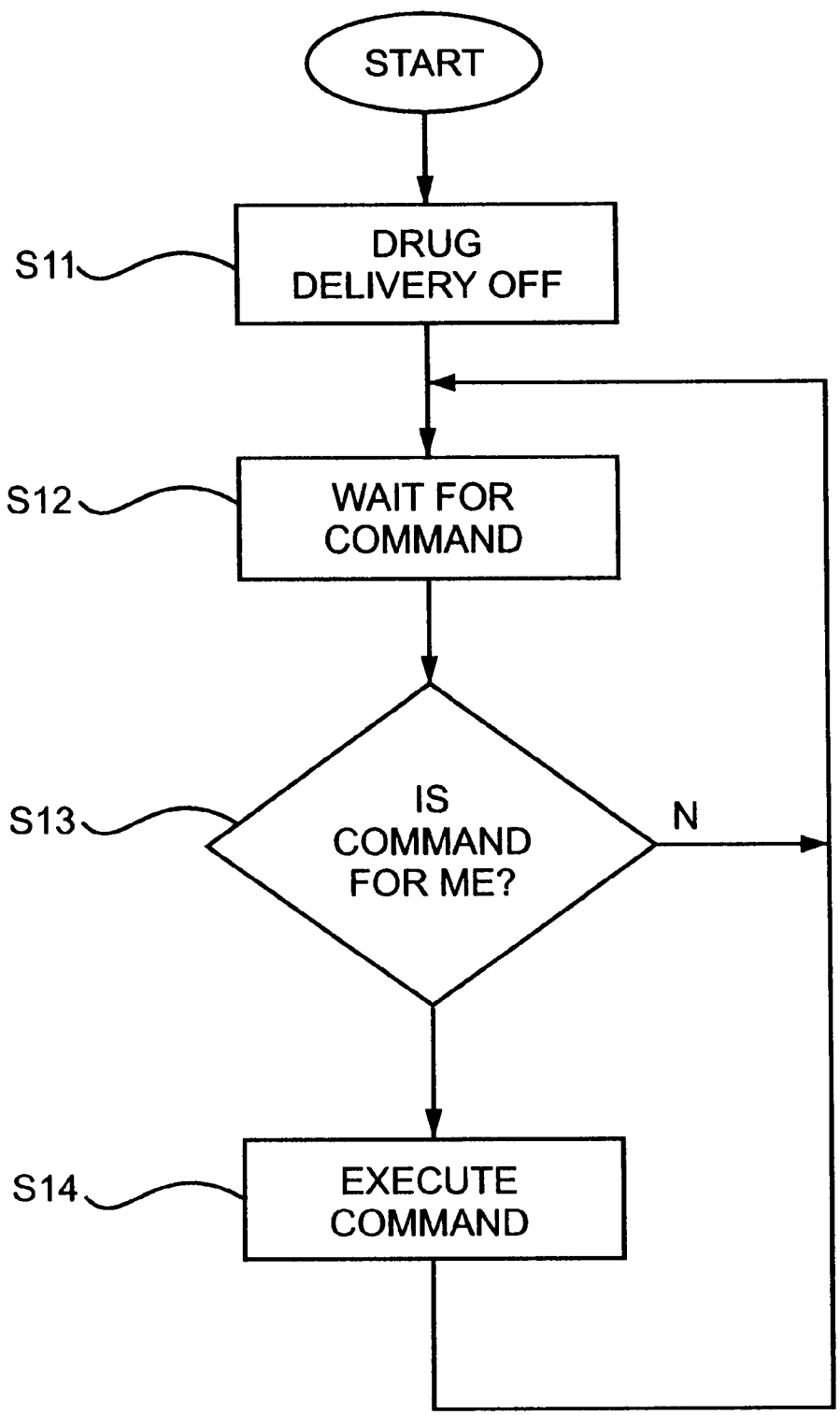
FIG. 6 is a flow chart depicting the operation of a slave controller in a master-slave configuration.

FIGS. 5 and 6 show the operation of a master and slave arrangement configuration for alternately delivering two drugs to a patient. This configuration uses one master unit and two slave units.

FIG. 5 depicts the operation of the master unit or controller in the master-slave configuration. After the master unit is turned on, it sends a stop command that stops all the slaves from delivering drugs in step S1. Next, in step S2 the master unit interrogates all of the slave units to identify which slave units are attached to the body. In this example, the master unit identifies a first controller for delivering a first drug and a second controller for delivering a second drug. Further, in this example, the first drug is delivered for one hour, followed by a one hour period during which no drug is delivered. Then, the second drug is delivered for three hours, followed by another hour during which no drug is delivered. This cycle is to be repeated four times, and then drug delivery is stopped.

After the initializing steps S1 and S2, the master unit starts the desired sequence of drug delivery in step S3 by sending a command to the first slave unit to start delivering drugs. The master unit then keeps track of time until one hour has passed, at which time it sends a command to the first slave unit instructing it to stop delivering drugs. Next, in step S4, the master unit keeps track of time until one hour has passed. In step S5, the master unit commands the second slave unit to start delivering its drug. The master unit keeps track of time until three hours have passed, at which time it sends a command to stop the second slave unit. Next, in step S6, the master unit waits for one hour to pass with no drug delivery. This completes a full cycle of drug delivery.

The master unit keeps track of the number of cycles of drug delivery that have been completed. In step S7, the master unit determines whether four drug delivery cycles have been completed. If four delivery cycles have not been completed, the master unit returns to the beginning of the routine for another cycle of drug delivery. When this cycle is complete, control returns to step S7. This continues until the master unit determines, in step S7, that four drug delivery cycles have been completed. When four delivery cycles have been completed, the master unit stops in step S8 and no further delivery of drugs occurs.

FIG. 6 depicts the control sequence of the slave unit in the master-slave configuration. When the slave unit is first turned on or otherwise activated, it turns off the delivery of drugs in step S11, and then proceeds to step S12 to wait for a command to arrive from the master unit. Some commands may be intended for the slave unit in question and other commands may be intended for other slave units. When a command arrives, the slave unit examines the command in step S13 and determines if the command is intended for itself. If the command is not intended for that particular slave unit in S13, the slave unit will not execute the command and will return to step S12 to wait for another command. If it is determined, however, that the command is intended for the particular slave unit in step S13, the slave unit executes the received command in step S14.

In one embodiment of the invention, the command from the master unit may simply instruct the slave unit to start or stop delivering drugs, with the dosage being preset for a given slave unit. In a more complex embodiment, the command from the master unit may contain information for setting the slave unit to deliver a desired dosage of drugs by appropriately setting the level of DC current.

The slave unit may also be programmed to acknowledge certain commands received from the master unit. When the slave unit receives this type of command, it transmits an acknowledgment signal back to the master unit. This acknowledgment signal could be a simple present/absent indication. Alternatively, it could report the status of the slave unit, including, for example, the amount of drugs remaining in the slave unit, the status of the slave unit battery, and other parameters. After executing the command in step S14, control returns to step S12, where the slave unit will wait for additional commands to arrive from the master unit.

Figure 7:
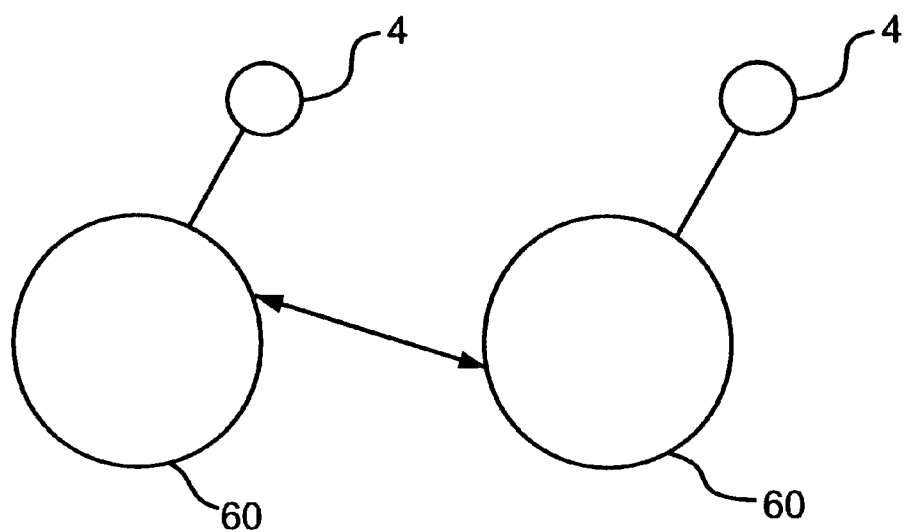
FIG. 7 is a diagram of a multi-master configuration of drug delivery devices.

FIG. 7 depicts a multi-master configuration of units or controllers. While FIG. 7 depicts two controllers 60, any number of controllers may be used. Each controller 60 has an associated patch 4 for delivery drugs to the patient. This configuration will be described in the context of delivering the same drug from multiple controllers, where the dosage of the drug is to be maintained constant regardless of the number of patches installed on the patient's body. In this configuration, when one patch is installed on the patient's body the dosage from each patch should be an amount "X"; when two patches are installed, the dosage from each patch should be X divided by 2; when three patches are installed, the dosage from each patch should be X divided by 3, and so on. This configuration could be used, for example, when a particular drug must be delivered constantly and where the dosage must be controlled with high accuracy. If a single controller were to be used in this application, a failure in that controller could interrupt the delivery of the drug. If independent controllers were used instead, a failure in any one controller might result in an incorrect drug dosage. By using a plurality of identical controllers that communicate with one another, these drawbacks can be eliminated and the desired drug dosage can be delivered.

Figure 8:
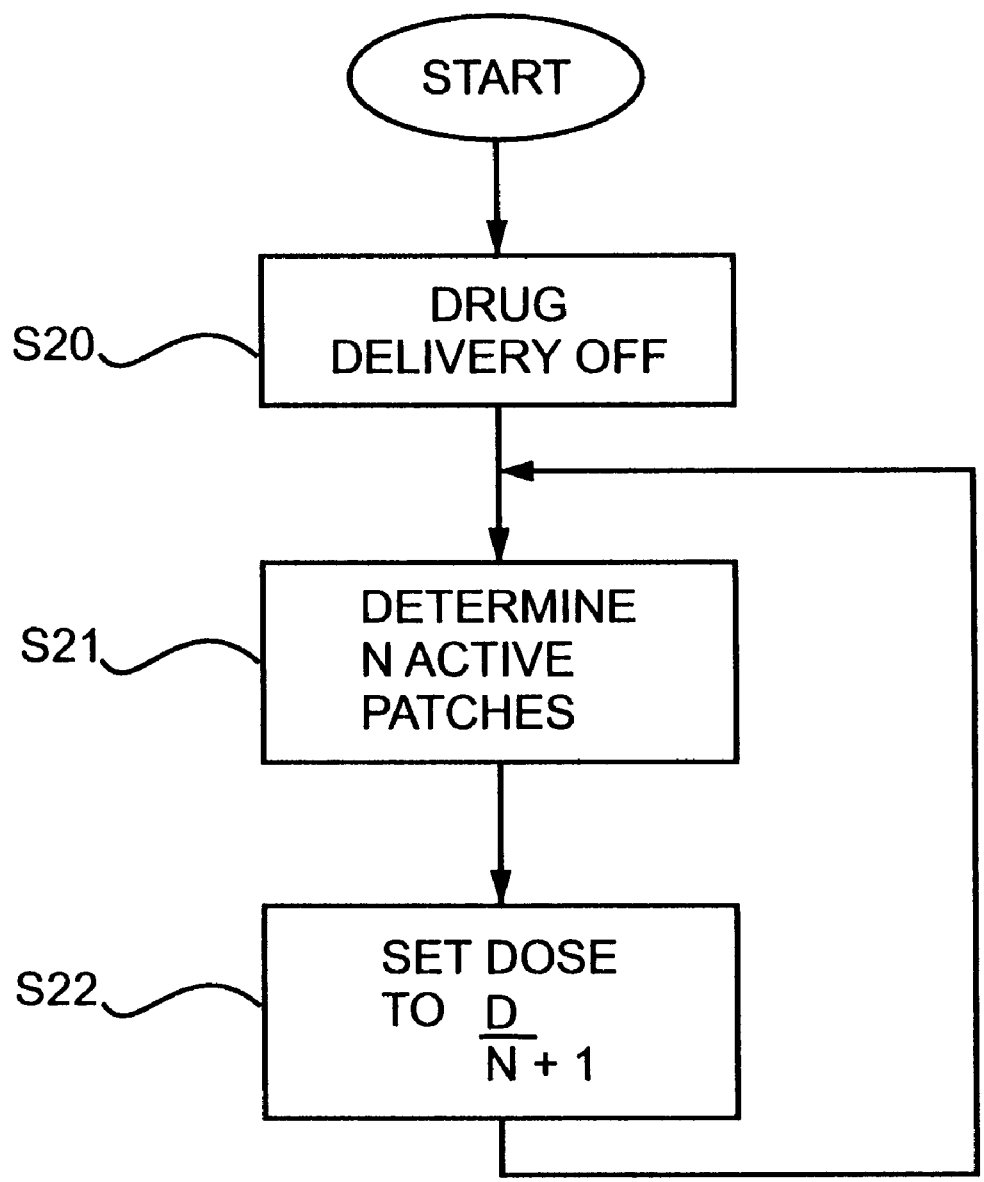
FIG. 8 is a flow chart depicting the operation of a controller in a multi-master configuration.

The operation of each of the multi-master units or controllers is depicted in FIG. 8. In this example, each of the controllers is programmed to adjust its drug output depending on how many other controllers are delivering drugs. When a given controller is first turned on, it stops the delivery of drugs in step S20. Next, in step S21, the controller sends and receives signals through the patient's body to determine a number of controllers (N) that are already delivering drugs to the patient. Then, in step S22, the controller sets its dosage to the desired total dosage (D) divided by N+1. The other controllers in the system will recognize that the new controller has been added when they execute their own step S21, and reduce their dosage from D÷N to D÷(N+1) in step S22. The final result is N+1 controllers each delivering a dosage of D÷(N+1), resulting in a total dosage of D.

Of course, it will be appreciated that the invention may take forms other than those specifically described. For example, instead of coupling the modulated AC carrier through the patch electrodes, the signal may be capacitively coupled into the patients' skin. Also, the master and slave units may be interconnected by wires and the like. In another embodiment, the master is a transmit-only device and each of the slaves is a receive-only device. In this embodiment, the demodulator 45 is not required in the master unit, and the modulator 43 is not required in each of the slave units.

While the preferred embodiments of the present invention have been described so as to enable one skilled in the art to practice the devices and methods of the present invention, it is to be understood that variations and modifications may be employed without departing from the concept and intent of the present invention as defined in the following claims. The preceding description is intended to be exemplary and should not be used to limit the scope of the invention. The scope of the invention should be determined only by reference to the following claims.

What is claimed is:

1. An apparatus for delivering drugs to a patient, comprising:
    a master controller including a transmitter for transmitting, into a first area of skin of the patient, a current comprising an AC component that travels along the patient's skin to a second area of skin of the patient, said master controller being affixable to the first area of skin; and
    at least one slave unit including a slave controller and a slave drug delivery device,
        said slave unit being affixable to the second area of skin,
        said slave controller including a receiver capable of receiving the AC component and an output signal connected to said slave drug delivery device, the output signal controlled in accordance with the received AC component, and
        said slave drug delivery device delivering a drug in accordance with the output signal.

2. The apparatus according to claim 1, wherein
    the transmitter of said master controller comprises a modulator for modulating an AC carrier with commands to be transmitted,
    the slave drug delivery device of said slave unit comprises an iontophoretic patch,
    the slave controller causes the patch to deliver drugs to the patient by passing a DC current through the patch, and
    the receiver of said slave unit comprises a demodulator for extracting the commands from the modulated carrier.

3. The apparatus according to claim 2, wherein the commands are coupled into the patient by superposing the modulated AC carrier with the DC current passing through the patch.

4. The apparatus according to claim 2, wherein the commands are coupled into the patient by capacitively coupling the modulated AC carrier into the patient's skin.

5. The apparatus according to claim 2, wherein the frequency of the AC carrier is the range of radio frequency or lower.

6. The apparatus according to claim 2, wherein the frequency of the AC carrier is greater than about 1000 Hz.

7. The apparatus according to claim 2, wherein the slave controller is capable of transmitting information to the master controller, and the master controller is capable of receiving the information.

8. The apparatus according to claim 2, further comprising a master drug delivery device comprising an iontophoretic patch, wherein the master controller causes the master drug delivery device to deliver drugs.

9. The apparatus according to claim 2, further comprising at least one additional slave unit.

10. An apparatus for delivering drugs to a patient, comprising:
    a first unit including a first drug delivery device and a first controller for causing the first drug delivery device to deliver a first drug, said first unit being affixable to a first area on the patient's skin; and
    a second unit including a second drug delivery device and a second controller for causing the second drug delivery device to deliver a second drug, said second unit being affixable to a second area on the patient's skin, said second controller selectively communicating with said first controller via AC signals that travel along the patient's skin between said first controller and said second controller.

11. The apparatus according to claim 10, wherein
    each controller includes a transmitter for transmitting signals, the transmitter comprising a modulator for modulating an AC carrier with commands to be transmitted, each controller includes a receiver for receiving signals, the receiver comprising a demodulator for extracting the commands from the modulated carrier, and
    each drug delivery device comprises an iontophoretic patch.

12. The apparatus according to claim 11, wherein the signals are coupled into the patient by superposing the modulated AC carrier with a DC current passing through the patch.

13. The apparatus according to claim 11, wherein the signals are coupled into the patient by capacitively coupling the modulated AC carrier into the patient's skin.

14. The apparatus according to claim 11, wherein the frequency of the AC carrier is the range of radio frequency or lower.

15. The apparatus according to claim 11, wherein the frequency of the AC carrier is greater than about 1000 Hz.

16. The apparatus according to claim 11, further comprising a third unit including a third drug delivery device and a third controller for causing the third drug delivery device to deliver a third drug, said third unit being affixable to a third area on the patient's skin, said third controller selectively communicating with said first controller and said second controller via signals that travel between said controllers.

17. An apparatus for delivering drugs to a patient, comprising:
    a drug delivery device, affixable to an area of skin of the patient;
    a controller for controlling the delivery of drugs from the drug delivery device;
    a transmitter for transmitting, into the area of skin, current comprising an AC component that travels along the patient's skin to other areas of skin; and
    a receiver capable of receiving, from the area of skin, current comprising an AC component transmitted by other apparatuses.

18. The apparatus according to claim 17, wherein the drug delivery device comprises an iontophoretic patch, the transmitter includes a modulator for modulating an AC carrier with commands to be transmitted, and the receiver includes a demodulator for extracting the commands from the modulated carrier.

19. The apparatus according to claim 18, wherein the commands are coupled into the patient by superposing the modulated AC carrier with a DC current passing through the patch.

20. The apparatus according to claim 18, wherein the signals are coupled into the patient by capacitively coupling the modulated AC carrier into the patient's skin.

21. The apparatus according to claim 18, wherein the frequency of the AC carrier is the range of radio frequency or lower.

22. The apparatus according to claim 18, wherein the frequency of the AC carrier is greater than about 1000 Hz.

23. A method of delivering drugs to a patient from multiple sites on the patient's body, comprising the steps of:

affixing a first drug delivery unit and a first controller to a first area of the patient's skin;

affixing a second drug delivery unit and a second controller to a second area of the patient's skin;

transmitting first information from the first controller to the second controller along the skin of the patient via current comprising an AC component;

receiving the first information at the second controller;

controlling a delivery of drugs from the first drug delivery unit in accordance with the first information; and controlling a delivery of drugs from the second drug delivery unit in accordance with the first information.

24. The method according to claim 23, further comprising the steps of:

transmitting second information from the second controller to the first controller along the skin of the patient via current comprising an AC component;

receiving the second information at the first controller;

controlling a delivery of drugs from the first drug delivery unit in accordance with the second information.

* * * * *